(12) United States Patent
Johnson et al.

(10) Patent No.: US 11,490,839 B2
(45) Date of Patent: Nov. 8, 2022

(54) FUNNEL WITH EXTENSION TUBE TO AUGMENT BLOOD COLLECTION DEVICE

(71) Applicant: Weavr Health Corp., Cambridge, MA (US)

(72) Inventors: Brandon T. Johnson, Cambridge, MA (US); Daniel Morgan, Salem, MA (US)

(73) Assignee: WEAVR HEALTH CORP., Cambridge, MA (US)

( * ) Notice: Subject to any disclaimer, the term of this patent is extended or adjusted under 35 U.S.C. 154(b) by 0 days.

(21) Appl. No.: 16/657,101

(22) Filed: Oct. 18, 2019

(65) Prior Publication Data

US 2020/0121233 A1 Apr. 23, 2020

Related U.S. Application Data

(60) Provisional application No. 62/810,416, filed on Feb. 26, 2019, provisional application No. 62/749,163, filed on Oct. 23, 2018.

(51) Int. Cl.
*A61B 5/15* (2006.01)

(52) U.S. Cl.
CPC .. *A61B 5/150061* (2013.01); *A61B 5/150022* (2013.01); *A61B 5/150755* (2013.01)

(58) Field of Classification Search
CPC ........ A61B 5/150061; A61B 5/150068; A61B 5/150343; G01N 33/4875;

(Continued)

(56) References Cited

U.S. PATENT DOCUMENTS

| 3,430,813 A | 3/1969 | Gilmont et al. |
| 3,767,085 A | 10/1973 | Cannon et al. |

(Continued)

FOREIGN PATENT DOCUMENTS

| EP | 2772306 A1 | 9/2014 |
| EP | 3088083 B1 | 8/2018 |

(Continued)

OTHER PUBLICATIONS

1/1-Designs Questel. APN-3020160043209 (2019.).

(Continued)

*Primary Examiner* — Devin B Henson
*Assistant Examiner* — H. Q. Nguyen
(74) *Attorney, Agent, or Firm* — Wilson Sonsini Goodrich & Rosati (57) ABSTRACT

A funnel-shaped extension attachment is provided for a blood collection device. The attachment provides a larger area for collecting a fingertip blood sample from a patient than the collection device itself would otherwise provide. The funnel is preferably easily removable from the collection device after the blood sample is taken. Optional trenches running down one or more corners of the attachment may be used to encourage pulling blood drops from the finger tip through capillary action. A tube may also provide another location to encourage pulling blood drops from the finger tip through capillary action. The funnel attachment may be mated with the collection device at a point of manufacture, or separately shipped and installed over the collection device at a point of use.

20 Claims, 7 Drawing Sheets

(58) Field of Classification Search
CPC ....... B01L 2400/0475; B01L 2300/045; B01L 3/508; B01L 3/50857
See application file for complete search history.

(56) References Cited

U.S. PATENT DOCUMENTS

| | | | |
|---|---|---|---|
| 4,185,628 | A | 1/1980 | Kopfer |
| 4,257,267 | A | 3/1981 | Parsons |
| 4,386,606 | A | 6/1983 | Tretinyak et al. |
| 4,558,793 | A | 12/1985 | Hansen |
| D284,214 | S | 6/1986 | Hatcher et al. |
| 4,690,005 | A | 9/1987 | Tervamaki et al. |
| 4,915,695 | A | 4/1990 | Koobs |
| 5,013,667 | A | 5/1991 | Lynn et al. |
| D324,426 | S | 3/1992 | Fan et al. |
| D331,807 | S | 12/1992 | Sodergren |
| 5,339,830 | A | 8/1994 | Blake, III |
| 5,384,264 | A | 1/1995 | Chen et al. |
| 5,504,011 | A * | 4/1996 | Gavin ............... G01N 33/4905 422/73 |
| 5,518,006 | A | 5/1996 | Mawhirt et al. |
| D410,287 | S | 5/1999 | Von Boetticher |
| D411,621 | S | 6/1999 | Eisen et al. |
| 6,093,156 | A | 7/2000 | Cunningham et al. |
| 6,106,779 | A | 8/2000 | Buechler et al. |
| 6,120,733 | A | 9/2000 | Goodman et al. |
| 6,372,514 | B1 | 4/2002 | Lee |
| 6,399,398 | B1 | 6/2002 | Cunningham et al. |
| 6,524,864 | B2 | 2/2003 | Fernandez Decastro |
| D512,512 | S | 12/2005 | Bell et al. |
| 7,404,931 | B2 | 7/2008 | Frey et al. |
| 7,435,237 | B2 | 10/2008 | Tan |
| D590,063 | S | 4/2009 | Garthoff et al. |
| 7,803,319 | B2 | 9/2010 | Yang et al. |
| 7,838,258 | B2 | 11/2010 | Yang et al. |
| D631,556 | S | 1/2011 | Shi et al. |
| 8,105,554 | B2 | 1/2012 | Kanigan et al. |
| 8,173,380 | B2 | 5/2012 | Yang et al. |
| 8,206,650 | B2 | 6/2012 | Samsoondar |
| 8,329,119 | B2 | 12/2012 | Pearcy et al. |
| D676,145 | S | 2/2013 | Kouge et al. |
| 8,561,795 | B2 | 10/2013 | Schott |
| 8,741,230 | B2 | 6/2014 | Holmes et al. |
| 8,808,202 | B2 | 8/2014 | Brancazio |
| 8,821,412 | B2 | 9/2014 | Gonzalez-Zugasti et al. |
| 8,827,971 | B2 | 9/2014 | Gonzalez-Zugasti et al. |
| 8,940,539 | B2 | 1/2015 | Pearcy et al. |
| 8,976,983 | B2 | 3/2015 | Jang et al. |
| D728,818 | S | 5/2015 | Burroughs et al. |
| 9,023,292 | B2 | 5/2015 | Rostaing et al. |
| 9,033,898 | B2 | 5/2015 | Chickering, III et al. |
| 9,040,236 | B2 | 5/2015 | Hill et al. |
| 9,041,541 | B2 | 5/2015 | Levinson et al. |
| D733,313 | S | 6/2015 | Kouge et al. |
| D734,482 | S | 7/2015 | Peterman et al. |
| 9,113,836 | B2 | 8/2015 | Bernstein et al. |
| 9,119,578 | B2 | 9/2015 | Haghgooie et al. |
| 9,176,126 | B2 | 11/2015 | Holmes et al. |
| 9,289,763 | B2 | 3/2016 | Berthier et al. |
| 9,295,417 | B2 | 3/2016 | Haghgooie et al. |
| 9,386,948 | B2 | 7/2016 | Holmes et al. |
| 9,427,184 | B2 | 8/2016 | Holmes et al. |
| 9,636,062 | B2 | 5/2017 | Holmes et al. |
| 9,987,629 | B2 | 6/2018 | Berthier et al. |
| D822,275 | S | 7/2018 | Moon et al. |
| D824,530 | S | 7/2018 | Velschow et al. |
| D855,210 | S | 7/2019 | Ito et al. |
| D861,189 | S | 9/2019 | Lampropoulos et al. |
| D861,915 | S | 10/2019 | Zakrys et al. |
| 10,488,424 | B2 | 11/2019 | Steckl et al. |
| 10,545,140 | B2 | 1/2020 | Cheng et al. |
| 10,597,651 | B2 | 3/2020 | Pottathil |
| D894,422 | S | 8/2020 | Johnson |
| D895,140 | S | 9/2020 | Heron |
| D895,146 | S | 9/2020 | Osmus et al. |
| 2002/0173047 | A1 | 11/2002 | Hudak et al. |
| 2003/0235825 | A1 | 12/2003 | Shea et al. |
| 2005/0119589 | A1 | 6/2005 | Tung et al. |
| 2005/0232813 | A1 | 10/2005 | Karmali |
| 2006/0228259 | A1 | 10/2006 | Samsoondar |
| 2007/0184547 | A1 | 8/2007 | Handique et al. |
| 2008/0025872 | A1 | 1/2008 | Dykes et al. |
| 2008/0118399 | A1 | 5/2008 | Fleming |
| 2008/0145835 | A1 | 6/2008 | Alajem et al. |
| 2009/0117665 | A1 | 5/2009 | Tung et al. |
| 2010/0099112 | A1 | 4/2010 | Zhou et al. |
| 2010/0210970 | A1 | 8/2010 | Horikawa et al. |
| 2010/0222703 | A1 | 9/2010 | Takashima et al. |
| 2011/0124984 | A1 | 5/2011 | Rostaing |
| 2011/0127294 | A1 | 6/2011 | Pearcy et al. |
| 2011/0143365 | A1 * | 6/2011 | Buchanan ............ B01L 3/5029 435/7.1 |
| 2011/0152720 | A1 | 6/2011 | Zappia et al. |
| 2011/0212453 | A1 | 9/2011 | Agarwal et al. |
| 2012/0168305 | A1 | 7/2012 | Hunter |
| 2013/0171044 | A1 | 7/2013 | Nikonorov et al. |
| 2013/0172698 | A1 | 7/2013 | Reynolds et al. |
| 2013/0211289 | A1 | 8/2013 | Moga et al. |
| 2013/0247694 | A1 | 9/2013 | Chen et al. |
| 2013/0280725 | A1 | 10/2013 | Ismagilov et al. |
| 2013/0309679 | A1 | 11/2013 | Ismagilov et al. |
| 2014/0050620 | A1 | 2/2014 | Johnson et al. |
| 2014/0073990 | A1 | 3/2014 | Holmes et al. |
| 2014/0273058 | A1 | 9/2014 | Menon et al. |
| 2014/0303518 | A1 | 10/2014 | Pierce et al. |
| 2014/0323911 | A1 | 10/2014 | Sloan et al. |
| 2014/0329258 | A1 | 11/2014 | Fleming |
| 2015/0069072 | A1 | 3/2015 | Kelley et al. |
| 2015/0231627 | A1 | 8/2015 | Sloan et al. |
| 2015/0273467 | A1 | 10/2015 | Sloan et al. |
| 2015/0346105 | A1 | 12/2015 | Gutsell et al. |
| 2016/0051981 | A1 | 2/2016 | Berthier et al. |
| 2016/0349156 | A9 | 12/2016 | Menon et al. |
| 2017/0023546 | A1 | 1/2017 | Holmes et al. |
| 2017/0042460 | A1 | 2/2017 | Holmes et al. |
| 2017/0108477 | A1 | 4/2017 | Ozbal |
| 2017/0176306 | A1 | 6/2017 | Boehm et al. |
| 2017/0227536 | A1 | 8/2017 | Matsuura |
| 2018/0043358 | A1 | 2/2018 | Fujimoto |
| 2018/0356393 | A1 | 12/2018 | Piasio et al. |
| 2019/0111421 | A1 | 4/2019 | Johnson |
| 2019/0126266 | A1 | 5/2019 | Johnson |
| 2019/0381499 | A1 | 12/2019 | Johnson |
| 2020/0121234 | A1 | 4/2020 | Johnson |
| 2020/0206743 | A1 | 7/2020 | Johnson |

FOREIGN PATENT DOCUMENTS

| | | |
|---|---|---|
| WO | WO-0167111 A2 | 9/2001 |
| WO | WO-03023371 A1 | 3/2003 |
| WO | WO-2012003306 A1 | 1/2012 |
| WO | WO-2017075050 A1 | 5/2017 |
| WO | WO-2017123668 A1 | 7/2017 |

OTHER PUBLICATIONS

A new era for blood collection and testing. Online, published date unkown. Retrieved on Nov. 18, 2019 from URL https://www.bostonmicrofluidics.com/.

Buckle. Online, published date Jun. 5, 2016. Retrieved on Nov. 22, 2019 from URL: http://www.8472.co.uk/misc_buckles_double.htm.

Garden House/Joaqufn Alvado Banon. Online, published date 2012. Retrieved on Nov. 22, 2019 from URL: https://www.archdaily.com/306750/garden-house-joaquin-alvado-banon.

PCT/US2018/056629 International Search Report and Written Opinion dated Jan. 22, 2019.

PCT/US2019/033878 International Search Report and Written Opinion dated Aug. 20, 2019.

PCT/US2019/033879 International Search Report and Written Opinion dated Oct. 25, 2019.

(56) References Cited

OTHER PUBLICATIONS

PCT/US2019/056918 International Search Report and Written Opinion dated Jan. 27, 2020.
PCT/US2019/056926 International Search Report and Written Opinion dated Jan. 24, 2020.
PCT/US2020/049460 International Search Report and Written Opinion dated Feb. 19, 2021.
Syringe Selection Guide, Complete Guide to Selecting the Right Hamilton Microliter, Gastight, and Specialty Syringes for your Application. Hamilton: 1-24 (2017).
Through the isosceles trapezoid window. Online, published date Dec. 6, 2006. Retrieved on Nov. 22, 2019 from URL: https://www.flickr.com/photos/page94/315753467.
U.S. Appl. No. 16/164,988 Non-Final Office Action dated Jul. 20, 2021.
U.S. Appl. No. 16/421,619 Non-Final Office Action dated Aug. 13, 2021.
U.S. Appl. No. 16/777,959 Final Office Action dated Aug. 10, 2021.
U.S. Appl. No. 16/242,084 Non-Final Office Action dated Jul. 16, 2021.
International Search Report and Written Opinion dated Jan. 9, 2020 for Related PCT/US19/056930.

\* cited by examiner

FUNNEL WITH EXTENSION TUBE TO AUGMENT BLOOD COLLECTION DEVICE

CROSS-REFERENCE TO RELATED APPLICATIONS

This application claims priority to a co-pending U.S. Provisional application entitled "Funnel with Extension Tube to Augment Blood Collection Device", Ser. No. 62/810,416, filed Feb. 26, 2019, and to a co-pending U.S. Provisional Application Ser. No. 62/749,163 filed Oct. 23, 2018 entitled "Locking Funnel to Extend a Sample Port in a Blood Collection Device", the entire contents of each of which are hereby incorporated by reference.

BACKGROUND

Technical Field

This patent relates to devices and methods for blood sample collection.

Background Information

Blood used for diagnostic testing is usually extracted from a patient with a hypodermic needle and collected in a test tube. The collected blood is then packaged for shipment to a remote lab where various diagnostic tests are performed. However, many diagnostic tests require significantly less volume than the actual collected sample. Separation of cellular components from the sample is also needed for some tests.

Many tests only require small blood samples, where a finger stick rather than a hypodermic needle can produce enough blood. But this small amount of blood cannot be easily transported to a remote lab. If the testing method cannot be immediately used at the same time the blood is extracted, convenient and reliable methods of collecting, prepping, and preserving small amounts of blood are still needed.

US Patent Publication US2014/0050620A1, assigned to Boston Microfluidics, Inc., describes several ways to implement a portable, user-friendly device for collecting a biological fluid sample and stabilizing it for transport to a remote lab. The devices may include a housing that provides a chamber for collecting a fluid sample. The housing itself, and/or mechanisms located within the housing, initiate collection of a predetermined, metered volume of a fluid sample. The devices may also stabilize the sample and/or seal the sample in the chamber. Other mechanisms in the device may mix the sample with a reagent.

SUMMARY

What is needed is a way for a user, such as patient or health care professional, to more easily introduce blood into a sample port of a blood sample collection device.

In one configuration, a locking, funnel-shaped attachment is provided for a blood collection device. The attachment provides a larger area for collecting a finger tip blood sample from a patient than the collection device itself would otherwise provide. In one embodiment, the funnel incorporates a tubular extension. The tubular extension provides assistance with collecting blood droplets from a fingertip via capillary action.

Optional trenches running down one or more corners of the funnel attachment may be used to further encourage pulling blood drops from the well.

The funnel is preferably easily removable from the collection device after the blood sample is taken.

The attachment may have flexible fingers extending away from the body of the funnel to grab or lock the well in position adjacent the sample port of the collection device. The fingers may then be spread away from the device to remove the funnel after the sample is taken.

The funnel attachment may be mated with the collection device at a point of manufacture, or separately shipped and installed over the collection device at a point of use.

DETAILED DESCRIPTION OF PREFERRED EMBODIMENTS

Figure 1A:
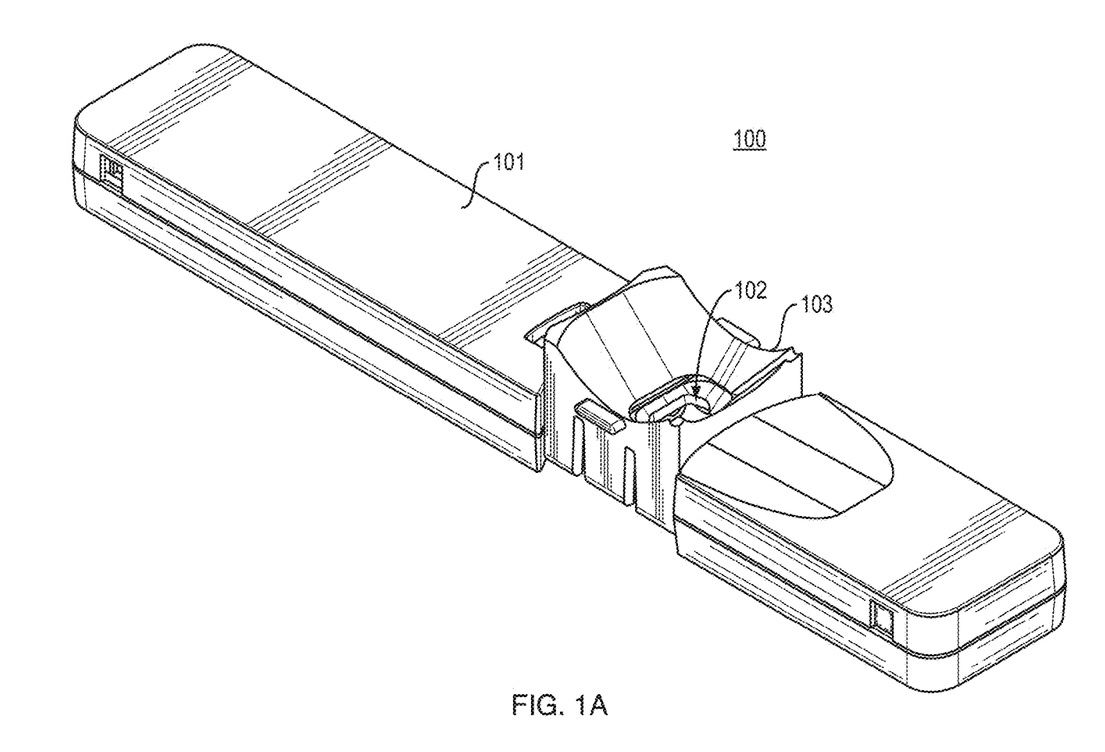
FIGS. 1A and 1B are respective isometric and side views of a blood sample collection device and funnel attachment.

FIG. 1A is an isometric view of an example blood collection device 100 that includes a two-piece housing 101, with a sample port 102. A removable locking funnel 103 is positioned over the sample port 102.

Figure 1B:
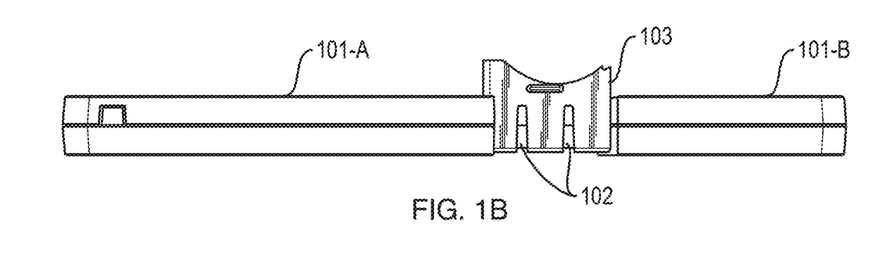

FIG. 1B is side view of the device 100 showing the sample port 102 between a first 101-A and second piece 101-B of the housing 101, and with the locking funnel 103 clipped over the sample port 102. Although the funnel 103 shown here has a generally rectangular (four-sided) shape with rounded corners, other shapes are possible.

Figure 2:
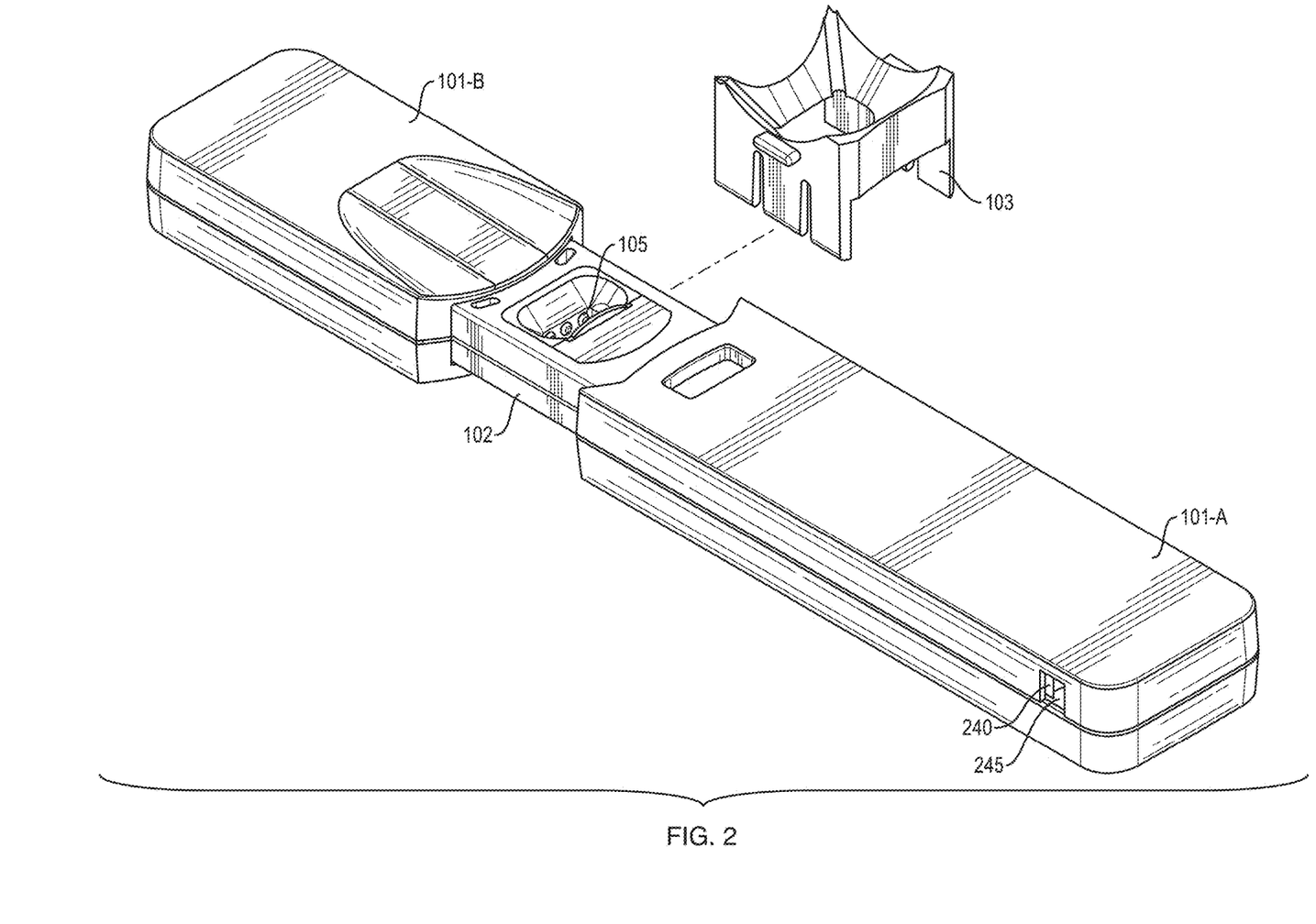
FIG. 2 is an isometric rendering taken from the opposite view angle, with the funnel removed, and with the collection device in an open position showing a sample port.

FIG. 2 is another isometric view of the device 100, taken from an opposite viewing angle, with the housing 101 still in the open position. Here the funnel 103 has been removed after the blood sample is introduced into the device 100. The sample port 102 is now seen more clearly.

FIGS. 1A, 1B and and 2 illustrate how the various components are arranged, with the housing 101 in an open position and the locking funnel 103 installed, before a blood sample is taken.

Figure 3:
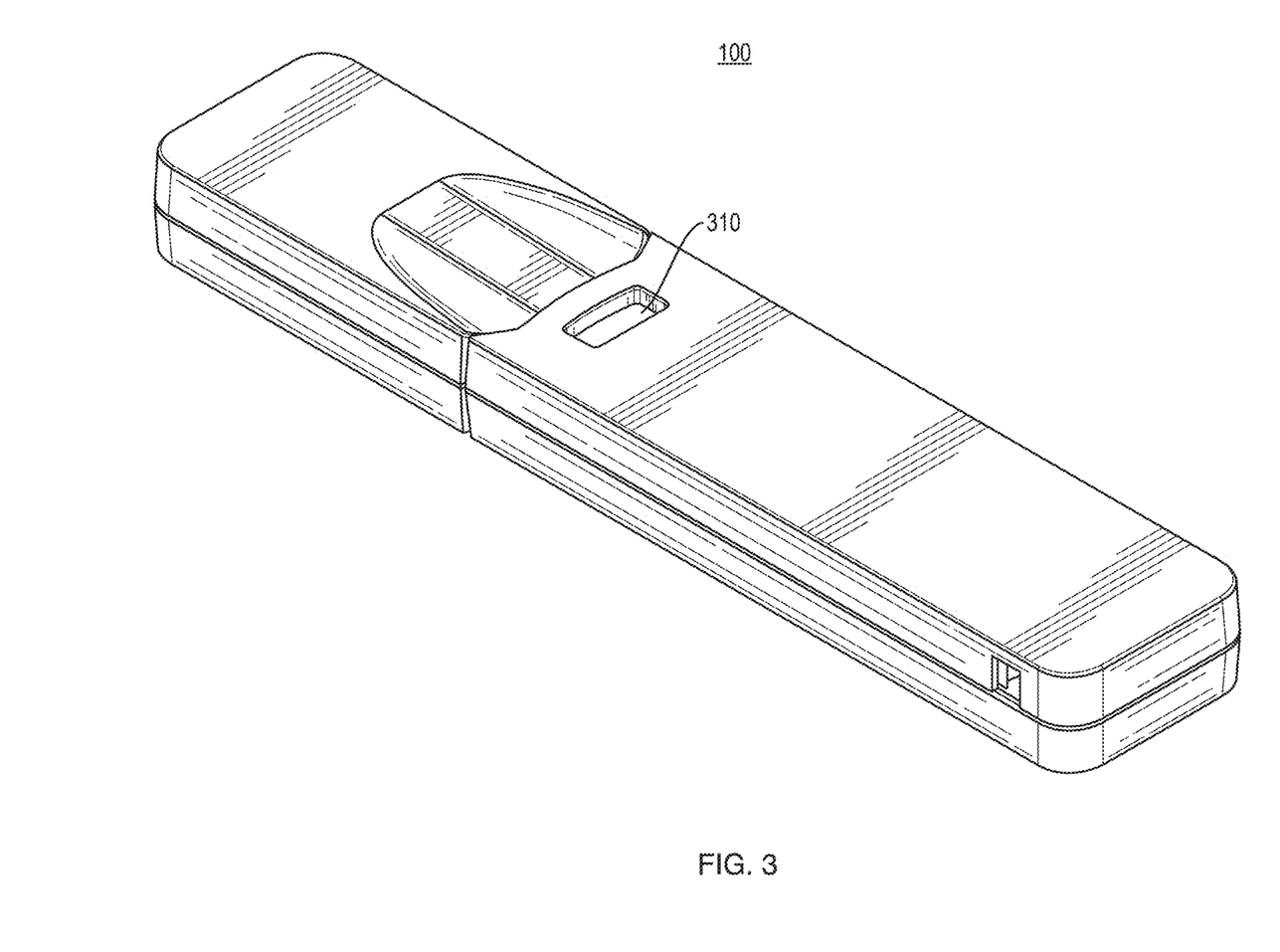
FIG. 3 is a view of the collection device in the closed position.

FIG. 3 is yet another view of the device 100, but now with the funnel attachment 103 having been removed, and with the two-piece housing 101 in the closed position. Note a window 300 in the housing permits the user to see one or more portions of the sample stored therein.

The device 100 is typically used as follows. The housing is presented in its open position, to provide access to the sample port 102. The funnel attachment 103 is clipped onto the housing, over the sample port. Installation of the funnel attachment 103 to the housing 101 may occur at time of assembly in a factory, or in the field at the time the sample is to be taken.

A user, such as a patient herself or a health care professional, then uses a lancet to produce a blood sample such as from a finger tip. Drops of whole blood are then taken with the finger positioned near to, above, adjacent to, or even in contact with the funnel 103 to minimize blood spillage. Blood flows from the funnel 103 down to the sample port 102, introducing whole blood into the rest of the device 101. As will be explained in more detail below for one embodiment, capillary action causes blood to flow from the sample port 102 into one or more collection capillaries 105 adjacent the sample port. The capillaries 105 can optionally be pre-coated with reagents such as heparin and/or EDTA for subsequent stabilization and preservation of the sample. The collection capillaries 105 can have a known and predetermined volume, in which case the incoming sample is precisely metered. The collection capillaries 105 then directed the metered sample to a collection media inside the device housing 101, as shown and described in more detail below.

The user, who can be the patient himself/herself or a healthcare professional, then manually removes (that is, unclips) the funnel 103 from the sample port 102. She then closes the device 100 by pushing the two housing pieces 101-A, 101-B together. The motion associated with closing the housing may then optionally enact one or more mechanisms that further process the sample now securely stored inside the device 100.

A window 300 in the housing may provide an indication of an amount of blood stored in the device, to permit the user to confirm status of the blood collection, such as whether the capillaries are drawing in blood, or whether a sufficient sample of blood is being drawn into (when the housing is in the open position) or was drawn into the device (when the housing is in the closed position).

Figure 4:
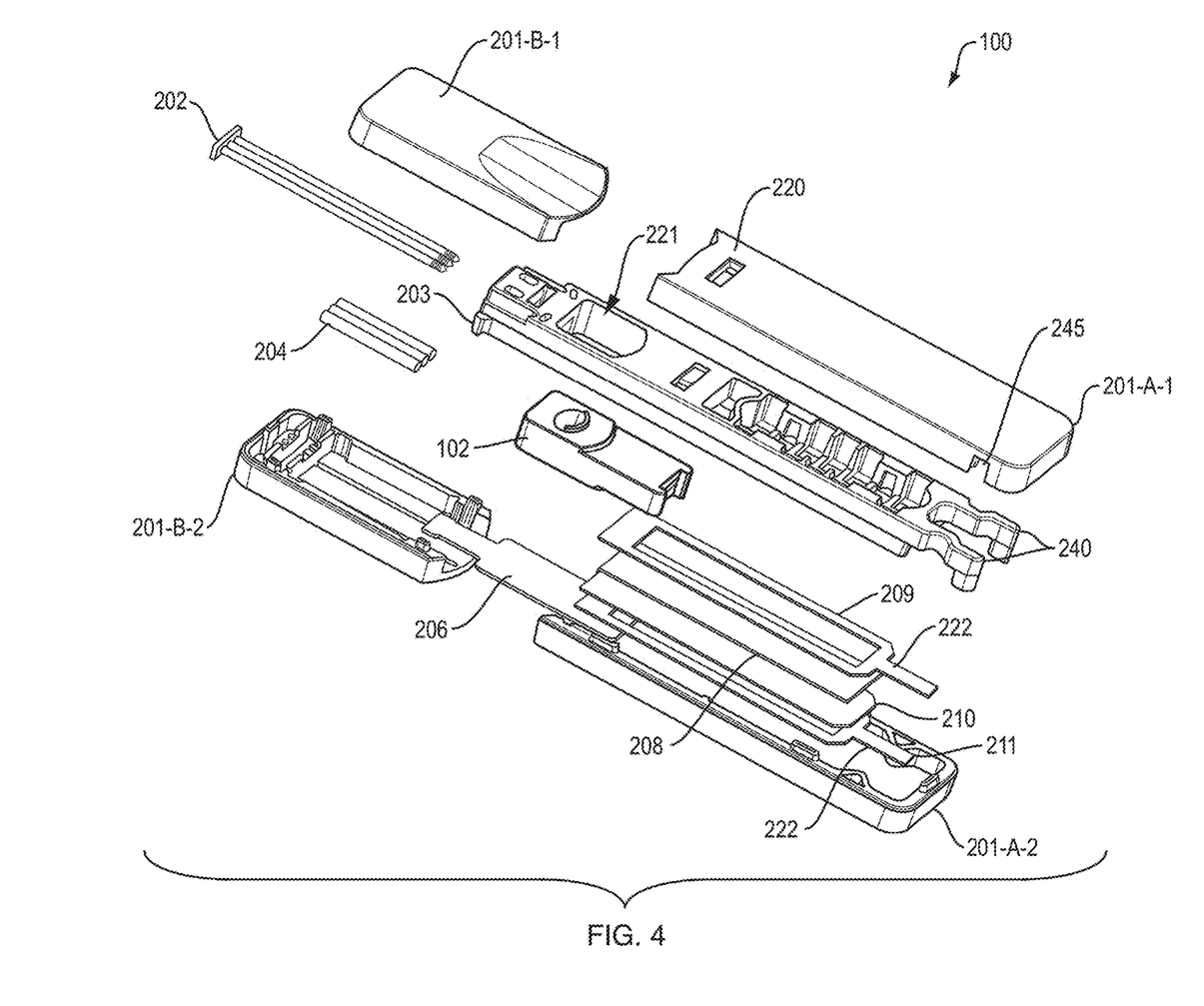
FIG. 4 is an exploded view showing components of one example of the collection device.
Figure 5A:
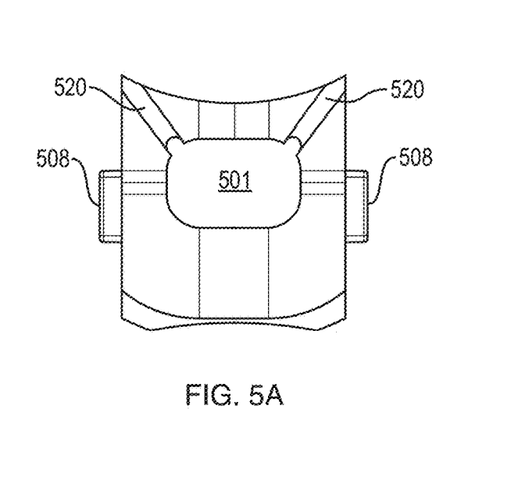
FIGS. 5A, 5B, 5C and 5D are top, side, front and isometric views of an example funnel attachment.
Figure 5B:
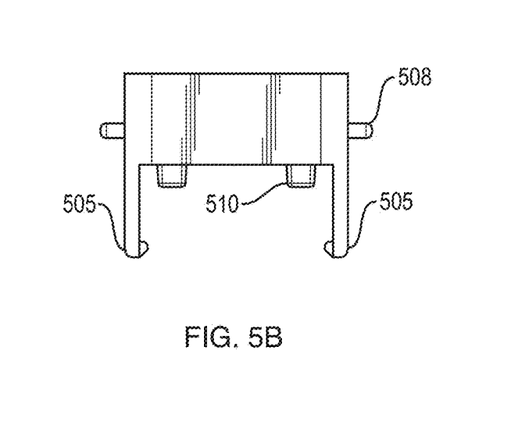
Figure 5C:
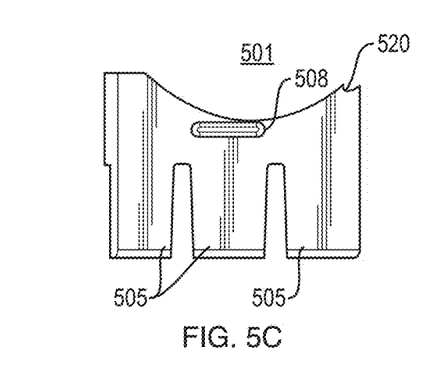
Figure 5D:
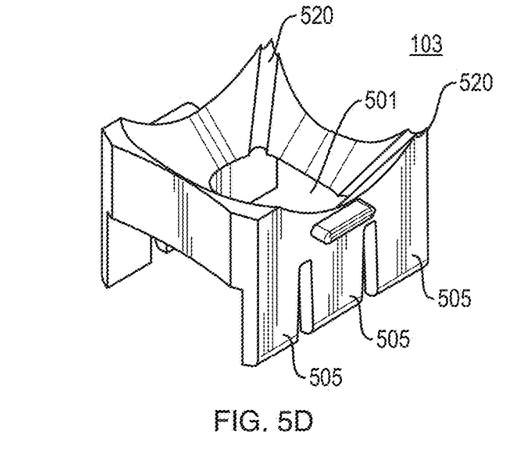

As seen in the exploded view of FIG. 4, the first housing piece 101-A consists of a top case 201-A-1 and bottom case 201-A-2, and second housing piece 101-B consists of a top case 201-B-1 and bottom case 201-B-2. A plunger rack 202 fits into a backbone structure 203. The backbone structure 203 may include a ribbed section to support a desiccant tablet (not shown) to further dry the collected sample. The backbone structure 203 may also provide a ratcheting housing closure mechanism (not shown in detail), which is activated when the two housing pieces 101-A, 101-B are pushed together.

Metering capillaries 204 engage the sample collection port 102 which may be further defined by a silicone inlay structure shaped to fit a hole 221 in backbone 203. The capillaries 204 can optionally be pre-coated with reagents, heparin, EDTA, or other substances.

A base 206 provides mechanical support for a blood collection membrane which may consist of a sample media 209. The sample media may be further supported and/or held in place by a top frame 208, mylar support 210, and bottom frame 211. The top 208 and bottom 211 frames may have extensions or tabs 222 on an outboard end. The tabs 222 assist with handling the media once it is removed from the housing 101.

The sample media 209 may be a pall membrane, an LF1 glass fiber membrane (sold by General Electric Company) or some other filter media designed to receive serum or whole blood which it then separates into a blood portion and a plasma portion. An LF1 paper's structure causes differential migration of the sample, with a slower rate for red cells, resulting in a gradual separation of plasma sample as it migrates down the paper.

The membrane 209 can optionally be previously impregnated with heparin, EDTA, sugars, or other stabilization agents.

In one arrangement, the plunger rack 202 firmly engages with the capillaries 204, creating a shutoff that blocks off any excess sample while also pushing the metered sample volume to the subsequent downstream steps.

It can now be appreciated that the action of closing the housing pieces together causes the sample to exit the capillaries and be deposited onto the sample media 209. In particular, each of the plungers 202 is aligned with a corresponding one of the capillary tubes 204. The capillary tubes 204 are in turn held in place within the silicone rubber inlay 102 through which the capillary tubes 105, 204 are visible in FIG. 2. As the housing sections are closed together, the plungers 202 are forced into the capillary tubes 204, which in turn force blood towards a slot in the collection element.

If a silicone inlay is used to define the sample port 102 it should have an elasticity that is sufficient to hold the capillary tubes 204 in place while the plungers 202 are forced into them. The elasticity of a silicone inlay 102 may also be chosen to seal the space around the capillary tubes and the inlay to prevent blood from flowing around the capillary tubes.

The closed housing also creates a small and isolated internal air space above the sample media 209. The sample can be further encouraged to dry quickly with the aid of one or more desiccant tablets supported by the backbone 203 adjacent where the sample media 209 sits when the housing is in the closed position.

During or after the closing action by the user, a ratcheting mechanism provided by tines 240 on the end of the backbone 203 encourage the housing to remain shut. For example, the tines 240 may act as a ratcheting pall and engage small holes 245 in the end of housing piece 101-A when the housing is pushed shut. The tines 240 may be shape to permit opening of the housing only with a special pinching tool that accesses small holes 245 in the side of the housing to releases the ratchet pawl. Thus, once the device 100 is closed, the blood sample remains enclosed within, largely cut off from the external environment, and ready for transport to a remote lab.

More details of the internal components of one example device 100, including the plunger, capillary tubes, silicone inlay, ratcheting pall and other features are found in our co-pending U.S. Provisional Patent Application Ser. No. 63/577,761 filed Oct. 27, 2017 entitled "Blood Metering and Storage Device", the entire contents of which are hereby incorporated by reference.

FIGS. 5A, 5B, 5C and 5D are more detailed top, side, front, and perspective views of the locking funnel 103. As explained above, this is preferably designed to be a removable attachment that fits over the top of the sample well 102. Locking funnel 103 extends access to the collection device, providing a larger area for collecting a finger tip blood sample than would otherwise be available.

The body of funnel 103 is generally rectangular, with four sides defining a bowl 501 into which blood from the patient is introduced. Two of the sides have downwardly extending, deformable fingers or clips 505 that are shaped to hold the funnel in place against the housing 101. Nibs 510, also located on the funnel adjacent where the funnel engages the port 102, may further assist with holding the funnel 103 in place.

Tabs 508 on the other two sides provide a place to assist with unclipping the funnel 103 from the housing 101.

The bowl 501, open on the bottom to permit blood to flow into the sample port 102, preferably has inwardly sloping walls at an angle of approximately 45 degrees from the vertical. However other bowl shapes, sizes, and slope angles are possible.

Optional trenches 520 extend down from one or more upper portions of the bowl 501. The user may swipe the finger tip against the trenches, to encourage pulling blood drops from the finger tip through capillary action. In one configuration, the trenches 520 are a 1 mm or 2 mm half-diameter pipe cut out of the sloping corners. The trenches 520 thus provide a way for the user to in effect cause trailing blood drops to be wicked away from the finger. They can thus help avoid blood spillage during the collection process.

The locking funnel 103 may be attached to or locked to the collection device 100 during manufacture and then removed after a blood sample is taken.

Figure 6A:
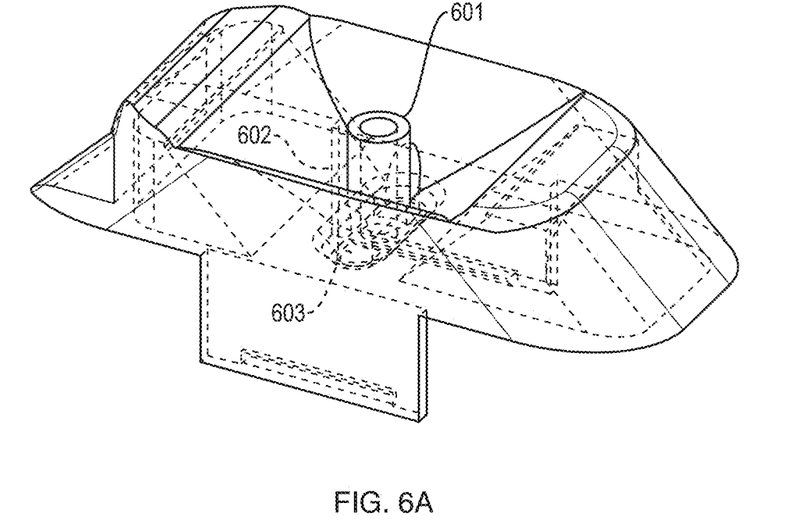
FIGS. 6A and 6B shows an alternate embodiment of an attachment that incorporates a tube.
Figure 6B:
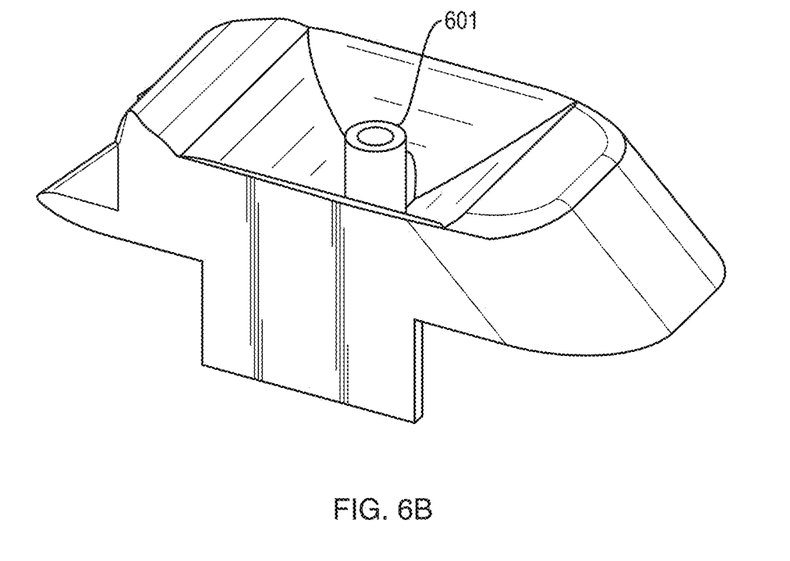

FIGS. 6A and 6B shown another arrangement of the locking funnel. Often times blood only flows in small droplets from a fingertip. In this arrangement, a tube 601 is provided in the center of the bowl and in fluid communication with an opening 603 in the bottom of the bowl. One or more support structures 602 within the funnel hold the tube 601 in position over opening 603. The top end of the tube 601 provides another location where the user may swipe their finger tip, to additionally encourage pulling blood drops from the finger tip through capillary action. In one configuration, the tube may be formed at the same time and of the same material as the rest of the funnel. The tube 601 thus provide a way for the user to in effect cause trailing blood drops to be wicked away from the finger. They can thus help avoid blood spillage during the collection process. The top end of the tube may have a sharp edge, as shown here, or may be rounded off (not shown).

Figure 6C:
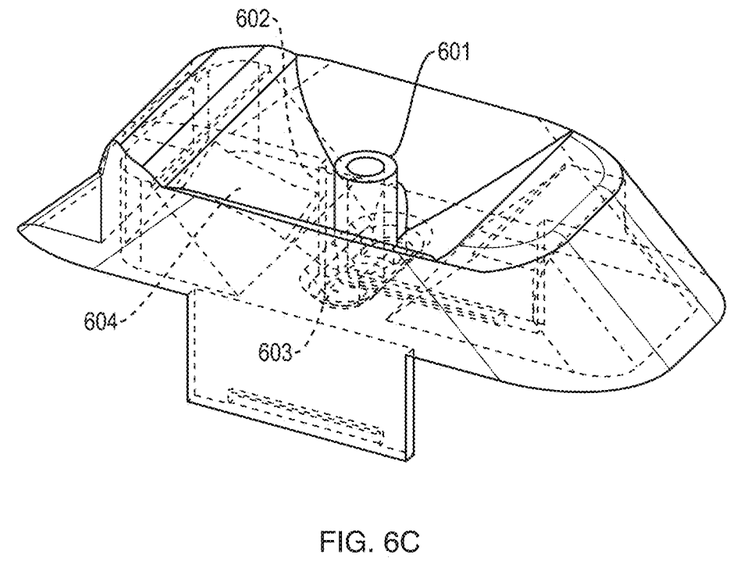
FIG. 6C shows a fluid containing pouch disposed between the device and the extension.

In some embodiments, a pouch containing an additional fluid may be attached or welded to portions of the device and/or the funnel near the collection well. One example is shown in FIG. 6C. The fluid contained in the pouch 604 may be a buffer, or a chaser, or a reagent that is released into the collection well when the funnel is attached or removed.

For example, when the funnel is attached to the device at the point of use, the pouch 604 may have been placed, during manufacture, in a location where attaching the funnel ruptures the pouch.

When the funnel is pre-installed on the device at the factory, the pouch 604 can be attached to both the device and the funnel, such that the pouch is ruptured when the funnel is removed from the device.

Either configuration permits the additional fluid to be added to the sample as it is drawn into the sample port and/or capillaries.

It should be understood that in light of the above, various modifications and additions may be made to the device without departing from the true scope of the inventions made.

The invention claimed is:

1. A biological sample collection device comprising:
   a housing having a first portion and a second portion, wherein the first portion or the second portion is slidable so as to transition the housing from an open position to a closed position;
   a sample collection port for receiving a biological sample when the housing is in the open position;
   a sample collection media in fluid communication with the sample collection port;
   a mechanically actuated fluid controller comprising a plunger, configured to dispense the biological sample onto the sample collection media when the housing is transitioned from the open to the closed position; and
   a removable extension for fitting adjacent to the sample collection port,
   wherein the removable extension provides a larger area for collecting the biological sample as compared to a collection area of the sample collection port, and
   wherein the removable extension is configured to prevent actuation of the mechanically actuated fluid controller when fitted adjacent to the sample collection port.

2. The device of claim 1, wherein the removable extension further comprises: one or more trenches extending from a top of the extension to an area adjacent the sample collection port, wherein the trenches are shaped to encourage pulling the biological sample through capillary action.

3. The device of claim 1, wherein the removable extension is removably coupled to the housing.

4. The device of claim 1, wherein the removable extension is a four sided funnel.

5. The device of claim 1, wherein the removable extension further comprises a rounded off edge.

6. The device of claim 5, wherein the fluid controller further comprises:
   one or more the capillaries having a predetermined volume disposed between the sample collection port and the sample collection media.

7. The device of claim 1, wherein the sample collection media is configured to store the biological sample.

8. The device of claim 7, wherein the biological sample is configured to be transported to a remote location for testing when stored in the sample collection media.

9. The device of claim 1, wherein the removable extension further comprises one or more deformable clips that are shaped to hold the removable extension in place against the housing.

10. The device of claim 9, wherein the removable extension comprises tabs configured to assist with unclipping the removable extension from the housing.

11. The device of claim 1, wherein the removable extension comprises rounded corners.

12. The device of claim 1, wherein the removable extension comprises one or more nibs.

13. The device of claim 1, wherein the removable extension is a four sided funnel with rounded corners.

14. The device of claim 1, further comprising a desiccant within the housing.

15. The device of claim 1, further comprising a reagent coating a surface of the device which contacts the biological sample.

16. A method of collecting a biological sample from a user comprising:
   providing a sample collection device having:
      a housing comprising a first portion and a second portion, wherein the first portion or the second portion is slidable so as to transition the housing from an open position to a closed position;
      a sample collection media in fluid communication with a sample collection port; and
      a mechanically actuated fluid controller comprising a plunger, configured to dispense the biological sample onto the sample collection media when the housing is transitioned from the open position to the closed position;

a sample collection port exposed for receiving the biological sample when the housing is in the open position; and a removable extension for fitting adjacent to the sample port configured to prevent actuation of the mechanically actuated fluid controller when fitted adjacent to the sample collection port;

introducing the biological sample from the user into the removable extension;

removing the removable extension from the sample collection device; and transitioning the housing from the open position to the closed position.

17. The method of claim 16, wherein introducing the biological sample comprises swiping the user's fingertip on the removable extension.

18. The method of claim 16, further comprising processing the biological sample within the device.

19. The method of claim 18, wherein processing the biological sample comprises at least one of drying the biological sample, treating the biological sample with a reagent, or separating plasma from the biological sample.

20. The method of claim 16, further comprising testing the biological sample in or on the device itself.

\* \* \* \* \*